US00PP21093P2

(12) United States Plant Patent
White et al.

(10) Patent No.: US PP21,093 P2
(45) Date of Patent: Jun. 22, 2010

(54) ***HELLEBORUS* PLANT NAMED 'BLT02'**

(50) Latin Name: ***Helleborus* L. hybrid**
Varietal Denomination: BLT02

(75) Inventors: Anthony Robin White, Hampshire (GB); Susan Barbara White, Hampshire (GB)

(73) Assignee: Amazing Breeders Company B.V., JG Aalsmeer (NL)

( * ) Notice: Subject to any disclaimer, the term of this patent is extended or adjusted under 35 U.S.C. 154(b) by 0 days.

(21) Appl. No.: 12/316,613

(22) Filed: Dec. 15, 2008

(51) Int. Cl.
*A01H 5/00* (2006.01)

(52) U.S. Cl. ..... Plt./439

(58) Field of Classification Search ..... Plt./439
See application file for complete search history.

*Primary Examiner*—June Hwu
(74) *Attorney, Agent, or Firm*—Jondle & Associates, P.C.

(57) ABSTRACT

A new *Helleborus* plant particularly distinguished by abundant, pink inflorescences, a compact and mounded plant habit and a vigorous growth habit, is disclosed.

1 Drawing Sheet

Genus and species: *Helleborus* L. hybrid.
Variety denomination: 'BLT02'.

BACKGROUND OF THE NEW PLANT

The present invention comprises a new and distinct cultivar botanically known as *Helleborus* L., and hereinafter referred to by the cultivar name 'BLT02'. The new cultivar originated from a hybridization made in March 2002 in Kilmeston, Alresford, Hampshire, United Kingdom. The female parent was the *Helleborus niger* plant Potters Wheel strain (unpatented), while the male parent was an unnamed plant of *Helleborus×sternii* Blackthorn group (unpatented). The seeds produced by the hybridization were sown in a greenhouse in Kilmeston in the United Kingdom in June 2002. A single plant selection was chosen for further evaluation and for asexual propagation in the February 2004 in Kilmeston in the United Kingdom.

'BLT02' was subsequently asexually propagated by in vitro propagation in Aalsmeer, The Netherlands for four and one-half years. The present invention has been found to retain its distinctive characteristics through successive asexual propagations.

Plant Breeder's Rights for this cultivar were applied for in Europe on Dec. 4, 2008. 'BLT02' has not been made publicly available more than one year prior to filing of this application.

SUMMARY OF THE INVENTION

The following are the most outstanding and distinguishing characteristics of this new cultivar when grown under normal horticultural practices in Aalsmeer, The Netherlands.

1. Abundant, pink inflorescences;
2. A compact and mounded plant habit; and
3. A vigorous growth habit.

DESCRIPTION OF THE PHOTOGRAPH

This *Helleborus* plant is illustrated by the accompanying photograph which shows overall plant habit including blooms, buds, and foliage of the plant; the colors shown are as true as can be reasonably obtained by conventional photographic procedures.

The photograph is of a whole plant about one-year-old, grown outdoors in Aalsmeer, The Netherlands.

DESCRIPTION OF THE NEW CULTIVAR

The following detailed description sets forth the distinctive characteristics of 'BLT02'. The data which defines these characteristics were collected from asexual reproductions carried out in Aalsmeer, The Netherlands. The plant history was taken on one-year-old plants in February and grown outdoors. Color readings were taken under natural light outdoors. Color references are primarily to The R.H.S. Colour Chart of The Royal Horticultural Society of London (R.H.S.) (2001).

DETAILED BOTANICAL DESCRIPTION

Classification:
- *Family.*—Ranunculaceae.
- *Genus and species.*—*Helleborus* L. Hybrid.
- *Common.*—Hellebore.
- *Variety name.*—'BLT02'.

Plant:
- *Plant and growth habit.*—Upright and vigorous with a compact and mounded plant habit.
- *Propagation.*—In vitro propagation by tissue culture.
- *Height.*—30 cm.
- *Width.*—20 cm to 30 cm.
- *Time to produce a finished plant.*—About 1 year.
- *Root habit.*—Vigorous root system.

Stems:
- *Aspect.*—Upright.
- *Length.*—30 cm.
- *Diameter.*—20 cm.
- *Internode length.*—0.1 mm.
- *Texture.*—Smooth.
- *Color.*—RHS 183C.

Leaves:
- *Type.*—Compound and palmate.
- *Arrangement.*—Alternate.
- *Length.*—20 cm.
- *Width.*—15 cm.
- *Leaflet length.*—5 cm to 10 cm.
- *Leaflet width.*—3 cm to 5 cm.
- *Leaflet shape.*—Lanceolate.
- *Leaflet apex.*—Acute.
- *Leaflet base.*—Rounded.
- *Leaflet margin.*—Serrate.
- *Leaflet texture* (*both upper and lower surfaces*).—Smooth.
- *Leaflet color.*—Immature leaf: Upper surface: RHS 133A. Lower surface: RHS 139C. Mature leaf: Upper surface: RHS 133A. Lower surface: RHS 139C.
- *Leaflet venation pattern.*—Reticulate.
- *Leaflet Venation color.*—Upper surface: RHS 183C and RHS 133B. Lower surface: RHS 183C and RHS 139C.
- *Petiole.*—Length: 10 cm to 15 cm. Diameter: 4.0 mm. Color: RHS 183C. Texture: Smooth.
- *Petiolule.*—Length. 1.0 cm. Diameter: 2.0 mm. Color: RHS 183C. Texture: Smooth.
- *Stipules.*—Absent.

Inflorescence:
- *Type.*—Loosely branched cyme (raceme) composed of single rounded flowers.
- *Flower diameter.*—5 cm.
- *Flower depth* (*height*).—2 cm.
- *Number of flowers per inflorescence.*—6 to 9.
- *Self cleaning or persistent.*—Persistent.
- *Flowering season.*—January through March.
- *Quantity of inflorescences on the plant.*—3 to 4, but depends on the age of the plant.
- *Fragrance.*—Absent.
- *Lastingness of inflorescences on the plant.*—About 3 months.
- *Diameter.*—20 cm.
- *Depth* (*height*).—20 cm to 25 cm.

Bud:
- *Height.*—2.0 cm.
- *Diameter.*—1.0 cm.
- *Shape.*—Ovate.
- *Color.*—RHS 70C.
- *Texture.*—Smooth.

Bracts:
- *Shape.*—Ovate.
- *Attachment.*—Sessile.
- *Length.*—1.0 cm to 2.0 cm.
- *Width.*—1.0 cm.
- *Apex.*—Acute.
- *Base.*—Rounded.
- *Margin.*—Slightly serrate.
- *Texture* (*both surfaces*).—Smooth.
- *Number per inflorescence.*—5 to 15.
- *Color.*—Upper surface: RHS 133A. Lower surface: RHS 139C.

Peduncle:
- *Shape.*—Round.
- *Length.*—15 cm to 20 cm.
- *Width.*—4.0 mm.
- *Texture.*—Smooth.
- *Color.*—RHS 183C.

Pedicel:
- *Length.*—2.0 cm to 7.0 cm.
- *Diameter.*—3.0 mm.
- *Texture.*—Smooth.
- *Color.*—RHS 183C.

Sepals:
- *Number.*—5.
- *Shape.*—Ovate.
- *Length.*—2.0 cm to 3.0 cm.
- *Width.*—1.5 cm.
- *Apex.*—Rotundate.
- *Base.*—Rotundate.
- *Margin.*—Entire.
- *Texture* (*both surfaces*).—Smooth.
- *Color.*—While opening, inside: RHS 63D and RHS 139C. While opening, outside: RHS 63D and RHS 59C and RHS 139C. Fully open, inside: RHS 63C and RHS 139C. Fully open, outside: RHS 63C and RHS 59A and RHS 139C.

Nectary:
- *Length.*—0.1 cm.
- *Width.*—0.1 cm to 0.2 cm.
- *Number per flower.*—13 to 14.
- *Arrangement.*—Whorl.
- *Shape.*—Tubular.
- *Color.*—RHS 144A.

Reproductive organs:
- *Stamens.*—Number: 40 to 50. Color: RHS 11D. Length: 3.0 mm. Width: 0.1 mm.
- *Anthers.*—Anther shape: Ovate. Anther length: 0.2 cm. Anther diameter: 0.1 cm. Anther color: RHS 11D. Pollen amount: None.
- *Pistils.*—Number: 5. Shape: Tuberculate. Length: 2.0 cm. Width: 0.1 cm. Color: RHS 70C.
- *Stigma.*—Length: 0.2 cm. Width: 0.1 cm. Color: RHS 155B.
- *Ovary.*—Shape: Lanceolate. Color: RHS 70C.

Fruit and seed set: None observed.

Disease and insect resistance: No particular resistance or susceptibility has been observed.

COMPARISON WITH PARENTAL AND COMMERCIAL CULTIVARS

'BLT02' differs from the female *Helleborus niger* plant Potters Wheel strain (unpatented) in that 'BLT02' has stems that are caulescent (both the leaves and the flowers are borne from the same stems), while the female parent has leaves that are borne on stems separate from the flowers. Additionally, 'BLT02' has stems that bear more than one flower, while the female parent has stems that bear only one flower per stem.

'BLT02' differs from the male parent an unnamed plant of *Helleborus×sternii* Blackthorn group (unpatented) in that 'BLT02' has 5 leaflets per leaf, while the male parent has 3 leaflets per leaf. Additionally, 'BLT02' has pinkish-purple flower buds and sepals, while the male parent has greenish-white flower buds and sepals.

'BLT02' differs from the commercial cultivar 'Pink Beauty' (unpatented) in that 'BLT02' has more intense pink inflorescences and more inflorescences per plant than 'Pink Beauty'.

We claim:

1. A new and distinct cultivar of *Helleborus* plant as described and shown herein.

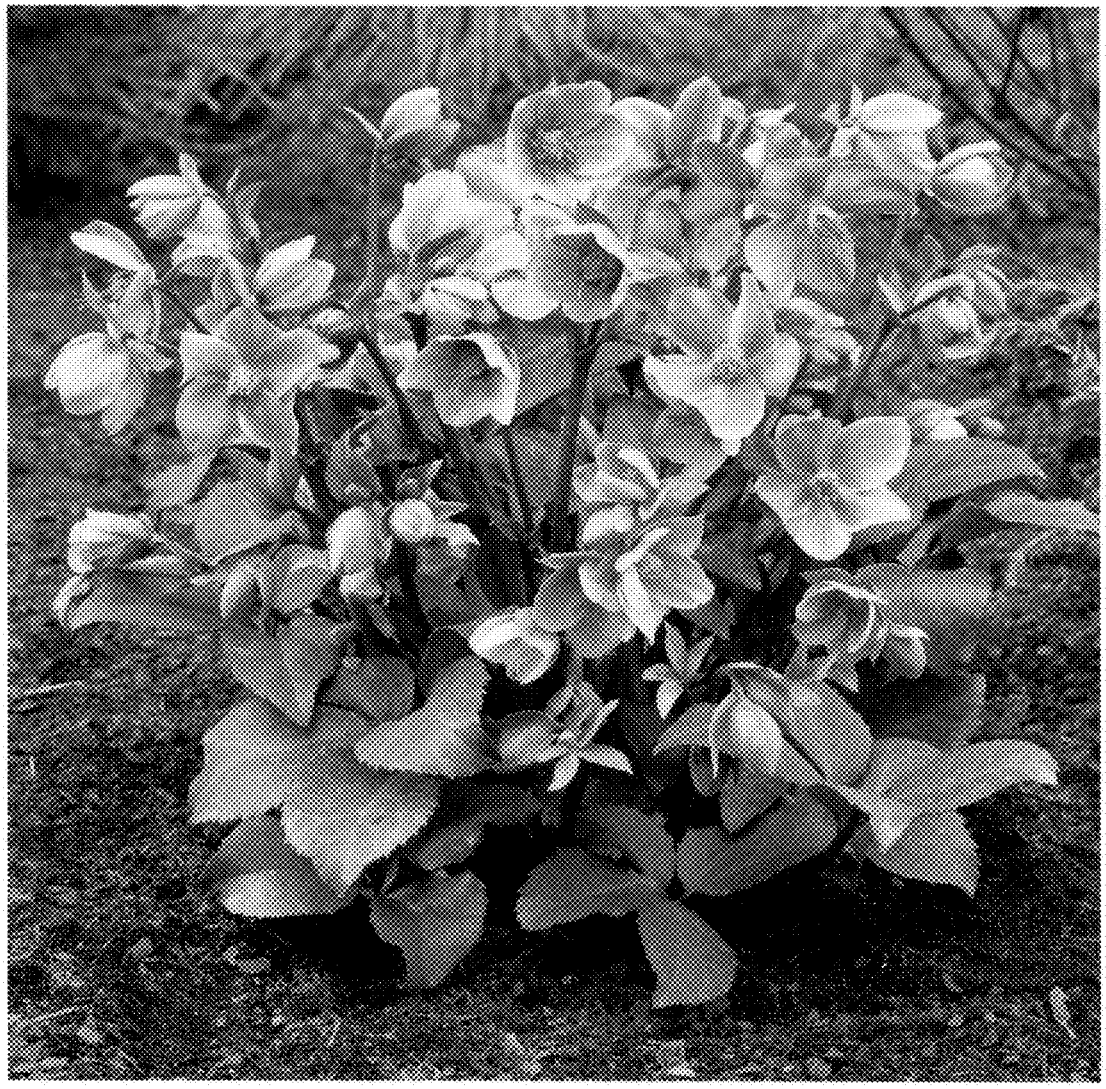

* * * * *